United States Patent
Gosney et al.

[19]

[11] Patent Number: 6,010,506

[45] Date of Patent: Jan. 4, 2000

[54] INTRAMEDULLARY NAIL HYBRID BOW

[75] Inventors: Mark Gosney, Memphis, Tenn.; Donna D. Holland, Atlanta, Ga.; Anthony James, Bartlett, Tenn.; John R. Pepper, Germantown, Tenn.; Thomas A. Russell, Memphis, Tenn.; Roy Sanders, Tampa, Fla.

[73] Assignee: Smith & Nephew, Inc., Memphis, Tenn.

[21] Appl. No.: 09/152,919

[22] Filed: Sep. 14, 1998

[51] Int. Cl.[7] ............................ A61B 17/56; A61B 17/58; A61F 2/30

[52] U.S. Cl. .................................................. 606/62; 606/63

[58] Field of Search .................................. 606/62, 63, 64, 606/60, 72, 73

[56] References Cited

U.S. PATENT DOCUMENTS

| | | |
|---|---|---|
| 3,846,846 | 11/1974 | Fischer . |
| 4,622,959 | 11/1986 | Marcus . |
| 4,776,330 | 10/1988 | Chapman et al. . |
| 4,805,607 | 2/1989 | Engelhardt et al. . |
| 4,827,917 | 5/1989 | Brumfield . |
| 4,858,601 | 8/1989 | Glisson . |
| 4,875,475 | 10/1989 | Comte et al. . |
| 4,940,467 | 7/1990 | Tronzo . |
| 4,995,883 | 2/1991 | Demane et al. . |
| 5,009,664 | 4/1991 | Sievers ........................................ 623/16 |
| 5,041,115 | 8/1991 | Frigg et al. ................................. 606/62 |
| 5,047,033 | 9/1991 | Fallin . |
| 5,108,452 | 4/1992 | Fallin . |
| 5,122,141 | 6/1992 | Simpson et al. . |
| 5,201,735 | 4/1993 | Chapman et al. .......................... 606/67 |
| 5,549,610 | 8/1996 | Russell et al. . |
| 5,569,249 | 10/1996 | James et al. . |

FOREIGN PATENT DOCUMENTS 1031128  of 0000  France .

*Primary Examiner*—Michael Buiz
*Assistant Examiner*—Vy Q. Bui
*Attorney, Agent, or Firm*—Garvey, Smith, Nehrbass & Doody, LLC

[57] ABSTRACT

An intramedullary nail apparatus includes an elongated nail body having a longer section and a shorter section. A detachable connection affixes the larger and shorter sections together end to end, using a taper lock connection, for example. The shorter section can provide transverse openings therethrough for enabling one or more fasteners to attach it to bone tissue, depending upon the medical indication. The nail includes a bow that consists of two tangent radii. This bow allows for the anterior bow of the femur and the relative straightness of the tibia. Thus, the apparatus of the present invention enables the same stems to be used in the treatment of femoral and tibial fractures. A stem is selected for any indication based on the desired diameter and length. The bow allows for a simplified surgical technique and a reduction in inventory of the nail system.

41 Claims, 4 Drawing Sheets

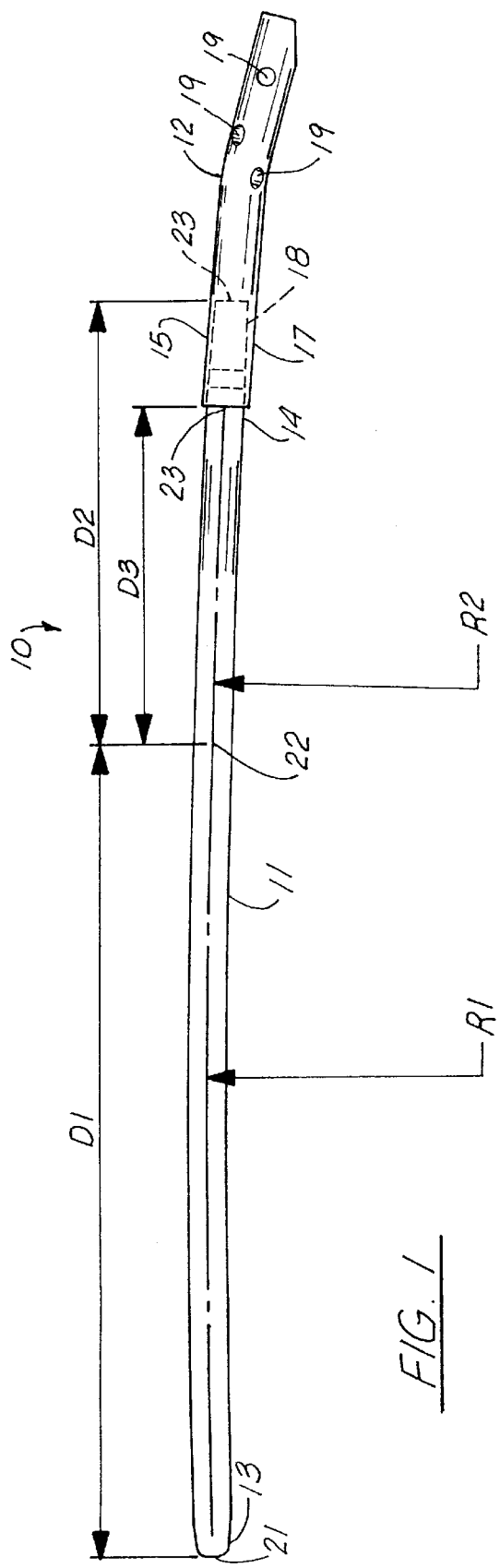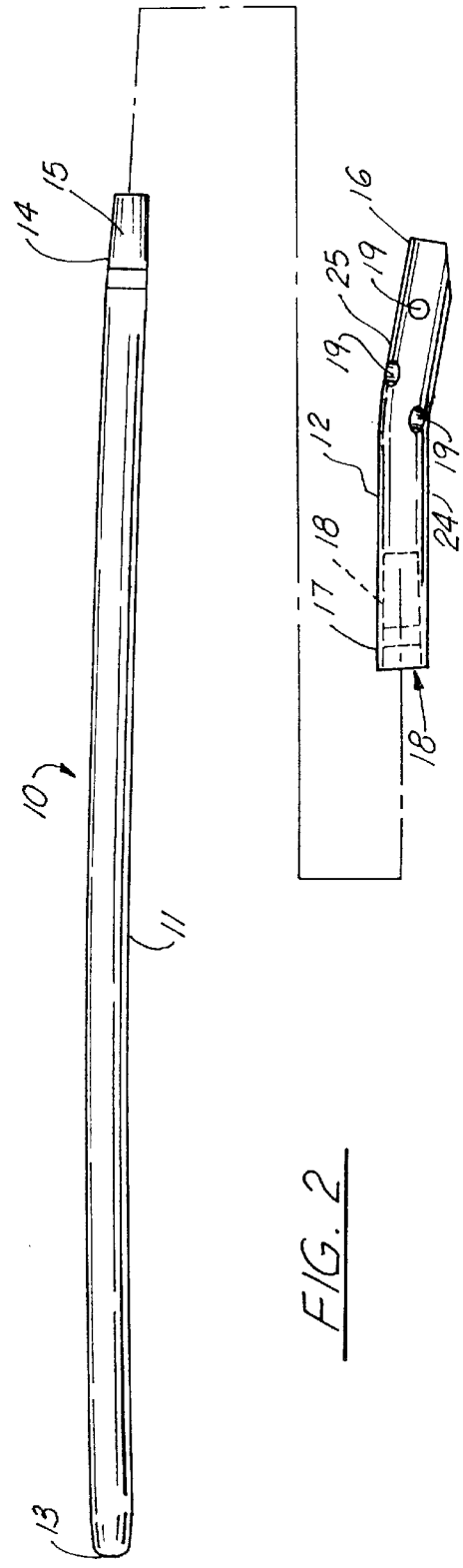
FIG. 1
FIG. 2

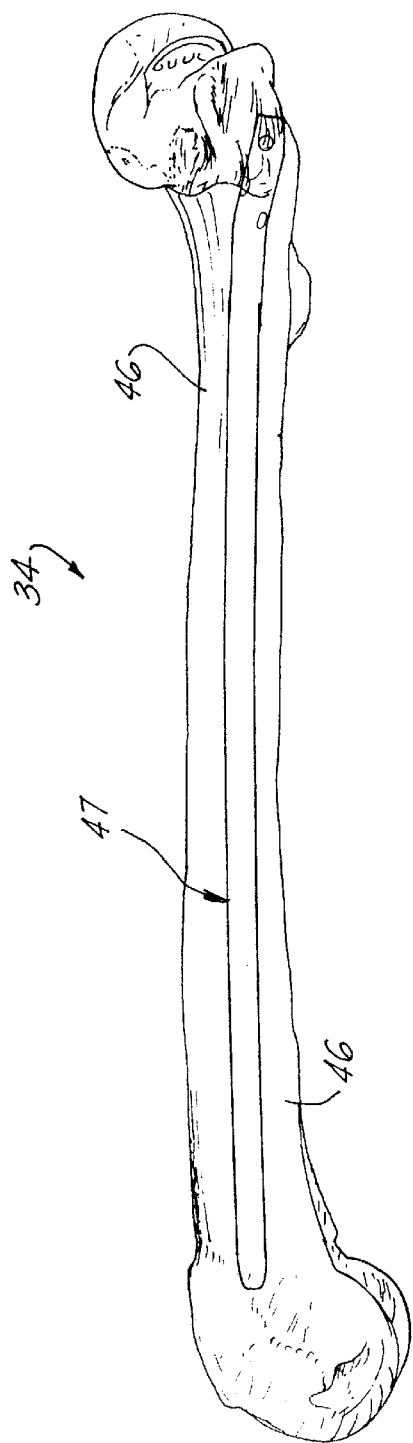
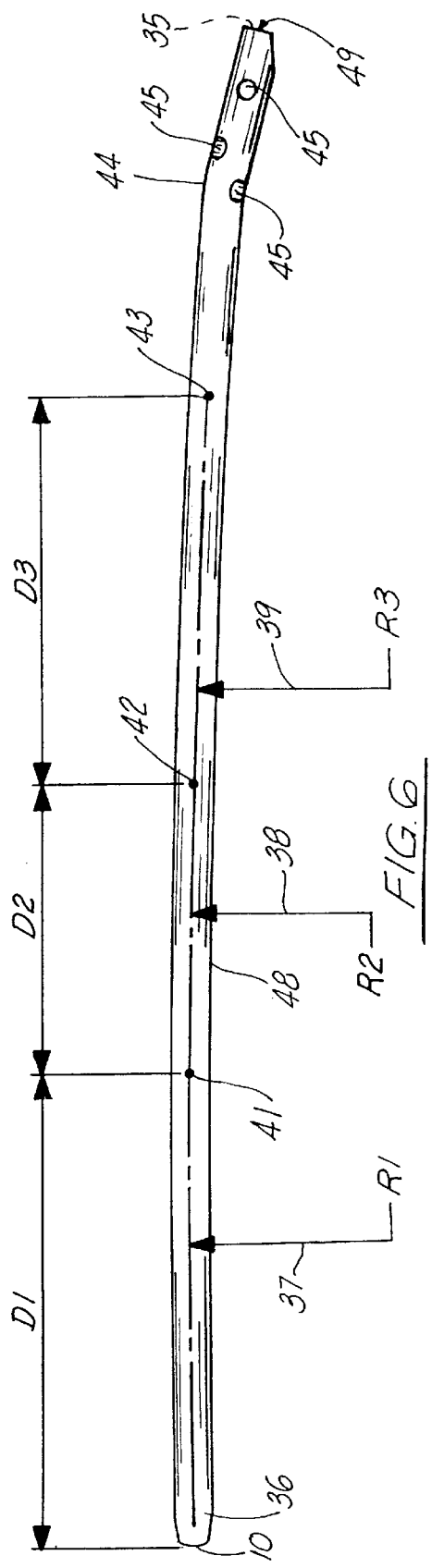
FIG. 5
FIG. 6

INTRAMEDULLARY NAIL HYBRID BOW

CROSS-REFERENCE TO RELATED APPLICATIONS

Not applicable

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to orthopaedic surgical devices, particularly intramedullary nails for surgical placement in a patient's long bone such as a tibia or femur. More particularly the present invention relates to an improved intramedullary nail that enables the same implant to be used in the treatment of either femoral and tibial fractures.

2. General Background of the Invention

Intramedullary nails have become the preferred implant treatment in many long bone fracture cases. As the use of intramedullary nails has become more popular, the design of the implants has advanced so that there are particular designs for different types of fractures. Nails having a particular configuration are desirable for certain indications. Because of wide variation of the long bones in patients, the particular style of nail is preferably available in a range of lengths, diameters, and shapes. As a result, the surgeon must have at hand a large inventory of styles and sizes to accommodate the variety of indications.

Currently, intramedullary nail systems include different nails for the treatment of femoral and tibial fractures. Intramedullary nails are designed to approximate the curvature of the particular bone. The femur has an anterior bow while the tibia is relatively straight. The nail curvature is achieved by a single radius or angle at a particular place. Femoral nails have a radius along a majority of the nail. Tibial nails have a straight midsection and bend angles at both ends to accommodate insertion.

Various intramedullary nail constructions have been patented. Such a system is taught in U.S. Pat. No. 4,805,607 to Engelhardt et al. where a modular intramedullary nail system has elongated base nails and extension members of different lengths and diameters. The base nail is the primary structural component of the system and the extension member is designed to fit on the proximal end of a base nail. By selecting various combinations of base nails and extension members, nails of a desired length and diameter can be constructed. The component parts are locked together by a pair of snap lock springs formed on the proximal end of the base nail, which include engagement tongs with locking barbs at the trailing end which are radially depressed in order to engage a counterbore on the extension member. A screw is inserted through a hole in the modular components after the rod has been implanted for preventing the tongs from disengaging.

Another intramedullary nail is disclosed in the Simpson et al. U.S. Pat. No. 5,122,141, entitled "Modular Intramedullary Nail". In the Simpson patent, an intramedullary nail system and method for providing a capability of creating intramedullary nails of any desired length includes a combination of a small number of base nail members adapted to be joined to any one of a variety of hollow extension nail members. Any selected extension nail member may be axially connected to any selected base nail member in order to prevent axially separation of the members. Additionally, each extension nail members provided with transverse openings adapted to receive a bone screw to secure the intramedullary nail within the bone to be repaired. The extension nail member is infinitely rotationally adjustable about the axis of the base nail member in order to enable the fixation of the extension member with any desired degree of anteversion prior to final assembly of the base nail member with the extension nail member.

The Comte et al. U.S. Pat. No. 4,875,475 shows a device for treating a bone that includes an intramedullary nail adapted to be driven into a hollow bone. The proximal terminal nail segment includes an internal thread and a transversely penetrating longitudinal slot adapted to receive a screw to penetrate through the nail, and to be screw connected to the bone. A distal terminal nail section comprises two transversely throughgoing bores, each adapted to receive a screw to be screw connected with the bone.

The Chapman et al. U.S. Pat. No. 4,776,330 discloses a modular femoral implant system for use in the treatment of femoral disorders resulting from injury, disease, or congenital defects. The modular system includes at least three interconnected components, including an elongated epiphyseal-metaphyseal implant, an intramedullary rod, and an angled side plate having an elongated plate portion adapted to be secured to the outer cortical wall, and a hollow sleeve adapted to extend into the femur.

A French Patent No. 1,031,128 relates to a femoral nail of multiple sections. The Fischer U.S. Pat. No. 3,846,846 discloses a ball-shaped portion to form part of the hip joint and a second portion that extends from the ball-shaped portion into the femur. The second portion is provided with a passage through which an elongated expander rod is extended which is also to be inserted into an opening in the femur and on the expanded rod is arranged a series of expansion elements in the form of a row which as the expander rod is moved longitudinally of the row are all expanded to anchor the prosthesis to the femur.

An adjustable compression bone screw is disclosed in the Glisson U.S. Pat. No. 4,858,601 that includes a shaft having first and second sections each with an external thread that may be rotated as a unit or independently. The screw includes means adapted to receive a first driving tool for driving the shaft as unit, and further adapted to receive a second driving tool for rotating the second section independently of the first section.

The Tronzo U.S. Pat. No. 4,940,467 discloses a variable length fixation device for insertion into a hole formed in two or more bone fragments and includes a barrel portion and a fastener element. The device is used for repair of the proximal portion of a patient's femur.

The Marcus U.S. Pat. No. 4,622,959, entitled "Multi use Femoral Intramedullary Nail", discloses an intramedullary nail for use in fractures for the left or right femur and includes a body having a head, an intermediate portion, and a distal tip. Transverse openings are provided in the body near the distal tip and in the head for receiving locking screws. One opening in the head has its axis within the femoral neck and another opening has its axis generally transverse thereto. The nail head has a seat with a transverse locating slot for securing a screw insertion tool in a fixed angular position in which the screw guide on the tool is aligned with one of the screw receiving openings.

The Brumfield U.S. Pat. No. 4,827,917, entitled "Femoral Fracture Device," provides an apparatus for treating fractures of the femur that includes a screw and an intramedullary rod. The screw has a threaded portion and a smooth portion. The rod has a head, stem, and longitudinal bore. There is at least one pair of coaxial holes through the stem, transverse to the longitudinal axis of the rod, for receiving first anchoring means such as a nail, screw, or bolt, to secure the rod within the marrow canal of the femur. There are at least a proximal pair of coaxial holes and a distal pair of coaxial holes in the head of the rod in an angled direction toward the femoral head relative to the longitudinal axis of the rod. The distal pair of head holes are adapted to slidingly receive the screw to permit the threaded portion of the screw, in use, to engage the femoral head and to allow sliding compression of a femoral neck or intertrochanteric fracture. An optional second anchoring means which will also allow sliding and compression and an optional set screw are also provided to adapt the fracture device to a variety of applications.

U.S. Pat. No. 4,995,883, issued to DeMane et al. and U.S. Pat. No. 5,108,452, issued to Thomas W. Fallin, both entitled "Modular Hip Prosthesis," disclose a modular hip prosthesis that can be custom fitted to a particular patient by a surgeon prior to surgical insertion. The prosthesis features a body having a neck portion for carrying a rounded head element, a transitional mid-section of the prosthesis body includes generally rectangular and generally rounded cross-sectional areas, and a stem section has a generally rounded cross-sectional area. The stem is tapered to receive a tubular extension sleeve with a hollowed portion corresponding in shape to the stem portion of the prosthesis. the tubular extension sleeve has an open end portion receptive of the lower tapering stem of the prosthesis body. The stem portion including an internal bore, and an attachment in the form of an elongated screw is provided for connection to the stem internal bore for securing the extension sleeve and the prosthesis body together, forming a compressive sealed connection therebetween. Pads can be attached to the transitional midsection of the prosthesis body for increasing the cross-sectional shape of the prosthesis at the transitional midsection. Removable collars can be added to the prosthesis to form a transverse load carrying interface with the upper end of the patient's femur. Frustoconically shaped extension sleeves can be added to the prosthesis neck for extending the neck length.

U.S. Pat. No. 5,047,033, issued to Thomas W. Fallin, entitled "Mill And Guide Apparatus For Preparation Of A Hip Prosthesis", discloses a guide apparatus for preparing the femur of a patient with a rotary mill to receive a femoral hip prosthesis includes a V-shaped guide body having a lower end base portion adapted to extend into the intramedullary canal of the femur and an upper end portion comprised of at least two spaced apart struts so that the overall guide body had a configuration substantially the same as the prosthesis body sought to be implanted in the patient. The lower end of the guide body base provides one or more hemispherical receptacles for holding the hemispherical end portion of a spinning mill bit. A preferably removable transverse guide rail has connection pins at one end portion thereto for forming a connection with the upper end of the guide body at one of the struts, the arm having a curved surface that is adapted to guide the mill bit during preparation of the intramedullary canal of the patient's femur for receiving a hip prosthesis thereafter.

U.S. Pat. No. 5,549,610, issued to James Russell et al., provides a femoral intramedullary nail with a distal nail section that is substantially longer than the proximal nail section.

U.S. Pat. No. 5,569,249, issued to Anthony James et al., discloses a cannulated modular intramedullary nail.

BRIEF SUMMARY OF THE INVENTION

The present invention provides an improved intramedullary nail apparatus that includes an elongated nail body having a longer section and a shorter section.

A detachable connection is provided for affixing the longer and shorter sections together end to end.

The shorter section has at least one transverse and/or oblique opening therethrough for accepting a fastener such as a threaded screw, bone screw, or the like. The longer section is curved along its length to provide a first curvature that extends a first distance that is greater than one half the length of the second section and a second curvature that extends a distance shorter than the first distance.

The first curvature has a radius of curvature that is greater than the radius of curvature of the second curvature and the nail body can be implanted into the intramedullary canal of either the femur or the tibia of a patient.

The first curvature has a radius of curvature of between about 110 and 130 inches.

The second curvature has a radius of curvature of between about 90 and 110 inches.

The first curvature extends a distance of between bout 2.5 and 12.0 inches of the length of the longer rod section.

The shorter nail section can be straight, as in the case of an antegrade femoral nailing.

The shorter section preferably can include two portions that form an obtuse angle as in the case of a tibial nail or a retrograde femoral nail. At least one of the rod sections has a longitudinally extended bore.

The shorter nail section provides a head portion that allows for interlocking for a particular indication. The longer nail portion is a stem portion that addresses the curvature and lengths of the nail.

The intramedullary nail of the present invention includes a hybrid bow that consists of two tangent radii. The hybrid bow allows for the anterior bow of the femur and the relative straightness of the tibia. With the apparatus of the present invention, the same stems can be used in the treatment of femoral and tibial fractures. A stem is selected for any indication based on the desired diameter and length. The hybrid bow configuration of the present invention allows for a simplified surgical technique and a reduction in inventory of the nail system.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein:

FIG. 1 is a elevational view of a first embodiment of the apparatus of the present invention showing a modular nail;

FIG. 2 is an exploded, elevational view of the first embodiment of the apparatus of the present invention;

FIG. 5 is a perspective view of a second embodiment of the apparatus of the present invention showing a one piece nail body implanted within a patient's femur; and FIG. 6 is a perspective view of the second embodiment of the apparatus of the present invention.

DETAILED DESCRIPTION OF THE INVENTION

Figure 3:
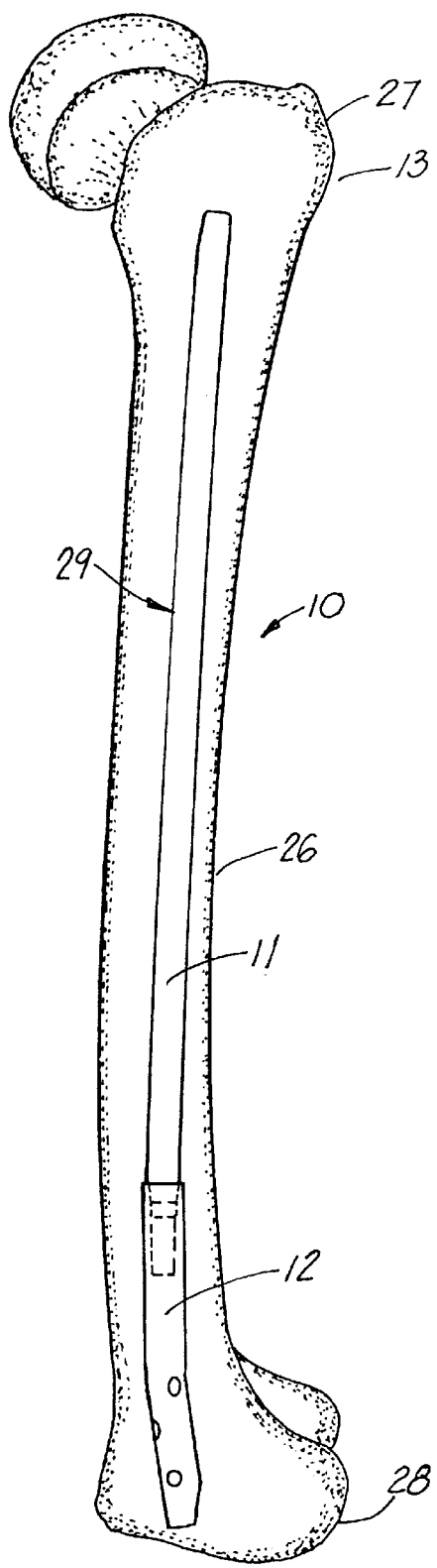
FIGS. 3–3A is a perspective view of the first embodiment of the apparatus of the present invention shown after implantation in a patient's femur.

A first embodiment of the apparatus of the present invention is designated generally by the numeral 10 in FIGS. 1–4. Intramedullary nail apparatus 10 includes a longer "stem" section 11 and a shorter "head" section 12. The longer section 11 provides a free end portion 13 and a connecting end portion 14. The connecting end portion 14 can include a frustoconical surface projecting portion 15. Shorter head section 12 has a free end 16 and a connecting end 17. The connecting end 17 can include a frustoconical socket 18. Openings 19 can be provided in the shorter head section 12 for receiving bone screws, pins and the like, depending upon the indication.

As shown in FIG. 1, the longer section 11 provides a bow or curve that consists of two tangent radii R1, R2. The radius R1 extends from the free end 13 of longer section 11 to a point nearer the middle portion of longer section 11. In FIG. 1, reference numerals 21 and 22 indicate the end portions of the first radius R1. The second radius R2 extends between the reference points 22 and 23. The tangent line drawn at point 22 is a tangent line for both curve portions of first radius R1 and second radius R2.

The first radius R1 provides a radius of curvature of about 120 inches and extends between reference points 21 and 22 by dimension D1. The dimension D1 is preferably between about 6.5 and 30 centimeters.

The radius of curvature R2 provides a radius of about 100 inches to define the radius that extends between reference points 22 and 23, preferably a distance D3 of about 3.0–3.5 inches. The dimension D3 is that dimension between reference point 22 and the connecting end 15 of longer section 11, preferably a distance of about 4.23 inches. The shorter or head portion 12 of nail 10 is comprised of first and second sections 24, 25, that form an obtuse angle of between about 168 and 176 degrees.

Figure 4:
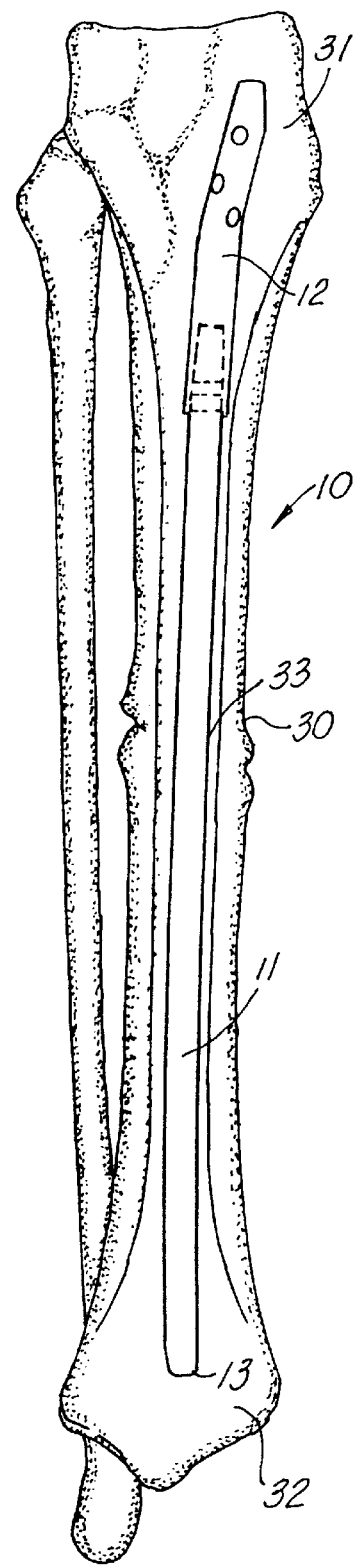
FIG. 4 is a perspective view of the first embodiment of the apparatus of the present invention illustrating implantation in a patient's tibia.
Figure 3A:
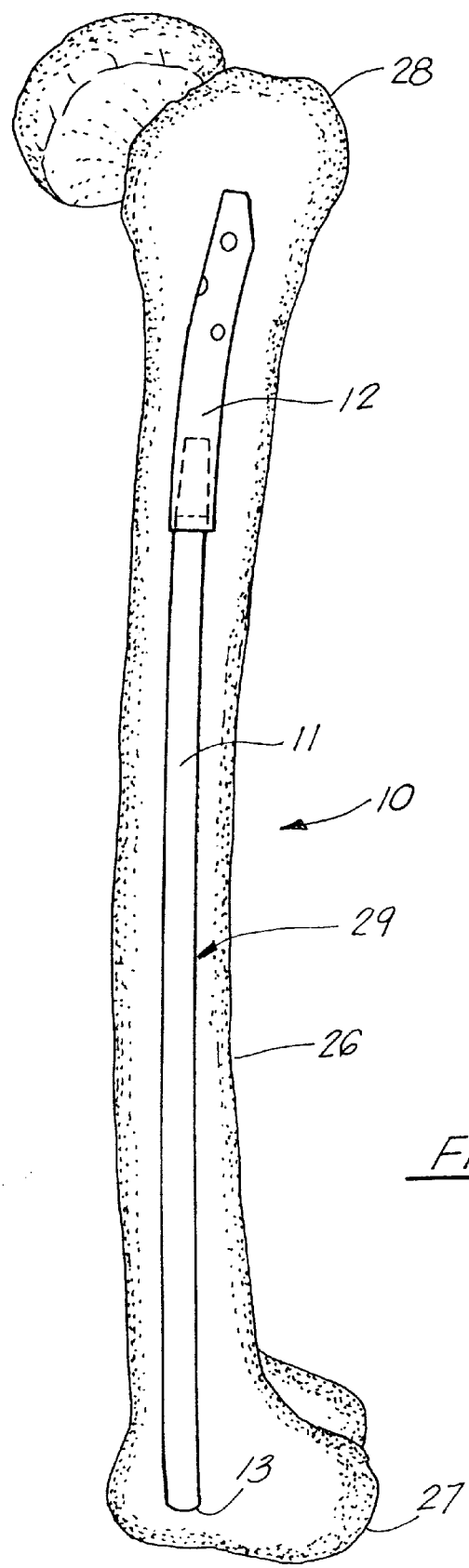

In FIGS. 3 and 4, the nail apparatus 10 of the present invention is shown after implantation in a patient's femur (see FIG. 3) and in a patient's tibia (see FIG. 4). In FIGS. 3–3A, the patient's femur 26 has an intramedullary canal 29 occupied by nail 10. Proximal 27 and distal 28 end portions of femur 26 are shown with respect to the intramedullary nail sections 11, 12. In FIG. 3, an antegrade placement is shown, as when nail 10 is implanted through the patient's hip. In FIG. 3A, a retrograde placement is shown when the nail 10 is implanted through the patient's knee. In FIG. 3, the longer section 11 and more particularly its free end 13 is positioned adjacent proximal femur 27. The shorter head section 12 is positioned adjacent the distal femur 28.

In FIG. 4, intramedullary nail apparatus 10 is placed in a patient's tibia 30. In FIG. 4, the shorter head section 12 of nail 10 is positioned adjacent the proximal tibia 31. The free end 13 of longer section 11 of nail 10 is positioned adjacent the distal tibia 32 as shown. The nail apparatus 10 occupies the tibial intramedullary canal 33 in FIG. 4.

FIGS. 5 and 6 show a second embodiment of the apparatus of the present invention designated generally by the numeral 34. Intramedullary nail 34 is an integral one-piece nail in the embodiment of the FIGS. 5 and 6. The nail apparatus 34 of the present invention includes an elongated nail body 48 having a proximal end 35 and a distal end 36. Nail body 48 is shown in intramedullary canal 47 of femur 46 in FIG. 5. In the embodiment of FIGS. 5 and 6, three separate curvatures are designated by the arrows 37, 38, and 39. The radius arrow 37 is for a radius of curvature that extends between reference points 40 and 41 and along the nail body 48 at distance D1. The second radius shown by the arrow 38 is a radius of curvature between reference points 41 and 42 that extends a distance D2. The third radius designated by arrow 39 in FIGS. 5 and 6 is a radius of curvature that extends between reference points 42 and 43 and along nail body 48 at distance D3.

The nail apparatus 34 can provide a straight section in between two sections with curvatures. The nail apparatus 34 can have three longitudinal sections, each having a curvature, and at least two of the curvatures being different curvatures. The radius R2 can be a straight longitudinal section positioned in between two sections with different curvatures.

The first radius of curvature 37 is preferably curved with a radius of curvature of between 110 and 130 inches. The second radius of curvature designated by arrow 38 is preferably curved with a radius of curvature of between 60 and 120 inches. The third radius of curvature designated by arrow 39 in FIG. 6 is preferably curved with a radius of curvature of between 60 and 120 inches. The distance D1 is preferably between about 6.5 and 30 inches.

The nail body 48 can be hollow, providing a longitudinally extending open ended bore 49. The nail body 48 can have a bend 44 at proximal end 35 as with the embodiment of FIGS. 1–4, including fixation openings 45.

The following is a list of suitable parts and materials for the various elements of the preferred embodiment of the present invention.

| PARTS LIST | |
| --- | --- |
| Part Number | Description |
| 10 | modular intramedullary nail |
| 11 | longer section |
| 12 | shorter section |
| 13 | free end |
| 14 | connecting end |
| 15 | frustoconical projecting portion |
| 16 | free end |
| 17 | connecting end |
| 18 | frustoconical socket |
| 19 | openings |
| 20 | reference point |
| 21 | reference point |
| 23 | reference point |
| 24 | first section |
| 25 | second section |
| 26 | femur |
| 27 | proximal femur |
| 28 | distal femur |
| 29 | intramedullary canal |
| 30 | tibia |
| 31 | proximal tibia |
| 32 | distal tibia |
| 33 | intramedullary canal |
| 34 | intramedullary nail |
| 35 | proxiinal end |
| 36 | distal end |
| 37 | arrow, radius of curvature |
| 38 | arrow, radius of curvature |
| 39 | arrow, radius of curvature |
| 40 | reference point |
| 41 | reference point |
| 42 | reference point |
| 43 | reference point |
| 44 | bend |
| 45 | opening |
| 46 | femur |

-continued

PARTS LIST

| Part Number | Description |
|---|---|
| 47 | intramedullary canal |
| 48 | nail body |
| 49 | open ended bore |
| R1 | first radius of curvature |
| R2 | second radius of curvature |
| D1 | first distance |
| D2 | second distance |
| D3 | third distance |

The foregoing embodiments are presented by way of example only; the scope of the present invention is to be limited only by the following claims.

We claim:

1. An intramedullary nail comprising:
   a) a one-piece, integral elongated nail body;
   b) a section of the nail body being curved along its length to provide at least two longitudinal sections with different curvatures including at least a first curvature that extends a first distance and a second curvature that extends a second distance, one of the curvatures having a radius of curvature of between 60 and 130 inches; and
   c) wherein a nail body will fit the intramedullary canal of either the femur or tibia.

2. The intramedullary nail of claim 1 wherein one end portion has a transverse or oblique opening.

3. The intramedullary nail of claim 1 wherein the nail body has a shorter section that has a transverse or oblique opening.

4. The intramedullary nail of claim 1 wherein the nail has three longitudinal sections with different respective curvatures.

5. The intramedullary nail of claim 1 wherein there is a straight longitudinal section in between the two sections with different curvatures.

6. The intramedullary nail of claim 1 wherein the nail body has a longer section and a shorter section and further comprising a detachable connection for affixing the longer and shorter sections together end-to-end.

7. The intramedullary nail of claim 6 wherein at least one of the sections has a longitudinally extended bore.

8. The intramedullary nail of claim 6 wherein the detachable connection includes cooperating projecting and socket portions.

9. The intramedullary nail of claim 1 wherein the nail body is a modular multi-part nail body.

10. The intramedullary nail of claim 1 wherein one of the curvatures has a radius of curvature between about 110 and 130 inches.

11. The intramedullary nail of claim 10 wherein the longer section has a longitudinally extended bore.

12. The intramedullary nail of claim 1 wherein one of the curvatures has a radius of curvature of between about 90 and 110 inches.

13. The intramedullary nail of claim 1 wherein one of the curvatures extends a distance of not more than 30 centimeters.

14. The intramedullary nail of claim 1 wherein one of the curvatures extends a distance of between 6.5 and 30 centimeters.

15. An intramedullary nail comprising:
   a) a nail body comprised of a long section and a short section;
   b) a section of the nail body being curved along its length to provide at least two longitudinal sections with different curvatures including at least a first curvature that extends a first distance and a second curvature that extends a second distance, one of the curvatures having a radius of curvature of between 60 and 130 inches;
   c) wherein a nail body will fit the intramedullary canal of either the femur or tibia
   d) wherein the nail body further comprises a detachable connection for affixing the longer and shorter sections together end-to-end; and
   e) wherein the shorter section includes two portions that form an obtuse angle.

16. The intramedullary nail of claim 15 wherein the shorter section has a longitudinally extended bore.

17. The intramedullary nail of claim 15 wherein the two longitudinal sections with different curvatures have tangent radii.

18. An intramedullary nail comprising:
   a) a one-piece, integral elongated nail body;
   b) a section of the nail body being curved along its length to provide at least two longitudinal sections with different curvatures including at least a first curvature that extends a first distance and a second curvature that extends a second distance, one of the curvatures having a radius of curvature of between 60 and 130 inches;
   c) wherein a nail body will fit the intramedullary canal of either the femur or tibia;
   d) wherein the nail body has a section and a shorter section and further comprising a detachable connection for affixing the longer and shorter sections together end-to-end; and
   e) wherein the shorter section includes two portions that form an obtuse angle of between about 184 and 192 degrees.

19. The intramedullary nail of claim 18 wherein the two longitudinal sections with different curvatures have tangent radii.

20. An intramedullary nail comprising:
   a) an elongated nail body having a longer section and a shorter section;
   b) a detachable connection for affixing the longer and shorter sections together end-to-end;
   c) the shorter section having at least one transverse opening therethrough;
   d) the longer section being curved along its length to provide a first curvature that extends a first distance and a second curvature that extends a second distance; and
   e) wherein the first curvature has a radius of curvature that is greater than the radius of curvature of the second curvature, and one of the curvatures is between 60 and 130 inches.

21. The intramedullary nail of claim 20 wherein the first distance is greater than one half of the length of the second section.

22. The intramedullary nail of claim 20 wherein the second distance is shorter than the first distance.

23. The intramedullary nail of claim 20 wherein the first and second curvatures have tangent radii.

24. An intramedullary nail comprising:
   a) an elongated nail body having a central axis and a longer section and a shorter section, said sections forming an obtuse angle;
   b) the shorter section having at least one opening therethrough that is transverse or oblique relative to the nail body central axis;

c) the longer section having two longitudinally extending curved sections of different curvature, the combined length of the two curved sections extending over a majority of the length of the longer section; and d) wherein one of the curved sections is of a greater length than the length of the other curved section, and one of a radius of the curvatures is between 60 and 130 inches.

25. The intramedullary nail of claim 24 wherein the nail has three longitudinal sections, each having a curvature and at least two of the curvatures being different curvatures.

26. The intramedullary nail of claim 24 wherein there is a straight section in between the two sections with curvatures.

27. The intramedullary nail of claim 24 wherein the nail body can be implanted in the intramedullary canal of either the femur or tibia of a selected patient.

28. The intramedullary nail of claim 24 wherein the combined length of the two curved sections is about equal to the length of the longer section.

29. The intramedullary nail of claim 24 wherein the two curved sections include a curved section with a larger radius of curvature that extends over at least half the length of the longer section.

30. The intramedullary nail of claim 24 wherein the shorter section occupies a position near the patient's distal femur when implanted in a patient's femur.

31. The intramedullary nail of claim 24 wherein the shorter section occupies a position near the patient's proximal femur when implanted in a patient's femur.

32. The intramedullary nail of claim 24 wherein the shorter section occupies a position near the patient's proximal tibia when implanted in a patient's tibia.

33. The intramedullary nail of claim 24 wherein the shorter section occupies a position near the patient's distal tibia when implanted in a patient's tibia.

34. The intramedullary nail of claim 24 wherein the shorter section occupies a position near the patient's distal femur when implanted in a patient's femur and wherein the shorter section further occupies a position near the patient's proximal tibia when implanted in a patient's tibia.

35. The intramedullary nail of claim 24 wherein the shorter section occupies a position near the patient's proximal femur when implanted in a patient's femur and wherein the shorter section further occupies a position near the patient's distal tibia when implanted in a patient's tibia.

36. The intramedullary nail of claim 24 wherein the shorter section occupies a position near the patient's distal femur when implanted in a patient's femur.

37. The intramedullary nail of claim 24 wherein the shorter section occupies a position near the patient's proximal tibia when implanted in a patient's tibia.

38. The intramedullary nail of claim 24 wherein the shorter section occupies a position near the patient's distal femur when implanted in a patient's femur and wherein the shorter section further occupies a position near the patient's proximal tibia when implanted in a patient's tibia.

39. An intramedullary nail comprising:

a) an elongated nail body having a longer section and a shorter section;

b) the shorter section having at least one transverse opening therethrough;

c) the longer section being curved along its length to provide a first curvature that extends a first distance that is greater than one half of the length of the second section and a second curvature that extends a distance shorter than the first distance;

d) wherein the first curvature has a radius of curvature that is greater than the radius of curvature of the second curvature, one of the curvatures having a curvature of between 60 and 130 inches; and e) the nail body can be implanted in the intramedullary canal of either the femur or tibia of a patient.

40. An intramedullary nail comprising:

a) an elongated nail body having a longer section and a shorter section;

b) a detachable connection for affixing the longer and shorter sections together end-to-end;

c) the shorter section having at least one transverse or oblique opening therethrough;

d) the longer section being curved along its length to provide at least two curvatures including at least a first curvature that extends a first distance and a second curvature that extends a second distance;

e) wherein the first curvature has a radius of curvature of between about 60 and 130 inches and the second curvature has a radius of at least 90 inches; and f) the nail body will fit the intramedullary canal of either the femur or tibia of a selected patient.

41. An intramedullary nail comprising:

a) a one-piece, integral elongated nail body;

b) a section of the nail body being curved along its length to provide at least two longitudinal sections with different curvatures including at least a first curvature that extends a first distance and a second curvature that extends a second distance, wherein the two longitudinal sections with different curvatures have radii that are tangent radii.

* * * * *